United States Patent
Choi et al.

(10) Patent No.: US 10,751,222 B2
(45) Date of Patent: Aug. 25, 2020

(54) HYDROPHILIC POLYURETHANE NANOFIBER AND METHOD FOR MANUFACTURING SAME

(71) Applicant: Kyungpook National University Industry-Academic Cooperation Foundation, Daegu (KR)

(72) Inventors: Jin Hyun Choi, Daegu (KR); Woo Jin Kim, Daegu (KR)

(73) Assignee: Kyungpook National University Industry-Academic Cooperation Foundation, Daegu (KR)

(*) Notice: Subject to any disclaimer, the term of this patent is extended or adjusted under 35 U.S.C. 154(b) by 0 days.

(21) Appl. No.: 16/076,942

(22) PCT Filed: Mar. 28, 2017

(86) PCT No.: PCT/KR2017/003298
§ 371 (c)(1),
(2) Date: Aug. 9, 2018

(87) PCT Pub. No.: WO2017/171341
PCT Pub. Date: Oct. 5, 2017

(65) Prior Publication Data
US 2019/0046361 A1    Feb. 14, 2019

(30) Foreign Application Priority Data
Mar. 29, 2016 (KR) .................. 10-2016-0037731

(51) Int. Cl.
*A61F 13/02* (2006.01)
*A61M 1/02* (2006.01)
(Continued)

(52) U.S. Cl.
CPC ........ *A61F 13/02* (2013.01); *A61F 13/00017* (2013.01); *A61L 15/22* (2013.01);
(Continued)

(58) Field of Classification Search
CPC ...... A61L 15/26; A61L 15/22; A61L 2400/12; C08L 75/04; A61F 13/00017;
(Continued)

(56) References Cited

U.S. PATENT DOCUMENTS

| | | | |
|---|---|---|---|
| 7,390,760 B1* | 6/2008 | Chen | A61F 13/514 442/340 |
| 2006/0094320 A1* | 5/2006 | Chen | A61F 13/514 442/340 |

FOREIGN PATENT DOCUMENTS

| | | |
|---|---|---|
| JP | 2002-143299 | 5/2002 |
| JP | 2014-055366 | 3/2014 |

(Continued)

OTHER PUBLICATIONS

Ji et al. (Analyst 2014;139:6467-6473. (Year: 2014).*
(Continued)

*Primary Examiner* — Ernst V Arnold
(74) *Attorney, Agent, or Firm* — Norton Rose Fulbright US LLP

(57) ABSTRACT

The present disclosure is to provide a method for producing polyurethane (PU) nanofibers with significantly improved hydrophilicity by producing water-soluble polymer/PU blend nanofiber by coaxial-electrospinning water-soluble polymer and hydrophobic PU, and, subsequently, dissolving and removing the water-soluble polymer from the blend nanofiber in water.

3 Claims, 7 Drawing Sheets

(51) Int. Cl.
| | | |
|---|---|---|
| *D04H 1/4358* | (2012.01) | |
| *D04H 1/728* | (2012.01) | |
| *B01D 39/16* | (2006.01) | |
| *D01D 5/34* | (2006.01) | |
| *D01F 8/10* | (2006.01) | |
| *D01D 5/00* | (2006.01) | |
| *D01F 8/16* | (2006.01) | |
| *A61L 15/26* | (2006.01) | |
| *A61F 13/00* | (2006.01) | |
| *A61L 15/22* | (2006.01) | |
| *A61M 1/34* | (2006.01) | |
| *D01F 6/70* | (2006.01) | |
| *C02F 1/00* | (2006.01) | |
| *D01F 6/14* | (2006.01) | |
| *A61M 1/36* | (2006.01) | |
| *A61M 1/00* | (2006.01) | |

(52) U.S. Cl.
CPC ............... *A61L 15/26* (2013.01); *A61M 1/02* (2013.01); *B01D 39/16* (2013.01); *B01D 39/1623* (2013.01); *D01D 5/003* (2013.01); *D01D 5/0007* (2013.01); *D01D 5/34* (2013.01); *D01F 8/10* (2013.01); *D01F 8/16* (2013.01); *D04H 1/4358* (2013.01); *D04H 1/728* (2013.01); *A61L 2400/12* (2013.01); *A61M 1/0088* (2013.01); *A61M 1/34* (2013.01); *A61M 1/3635* (2014.02); *B01D 2239/025* (2013.01); *B01D 2239/0421* (2013.01); *C02F 1/001* (2013.01); *C02F 2305/08* (2013.01); *D01F 6/14* (2013.01); *D01F 6/70* (2013.01)

(58) Field of Classification Search
CPC ....... A61F 13/02; A61M 1/0088; A61M 1/02; A61M 1/34; A61M 1/3635
See application file for complete search history.

(56) References Cited

FOREIGN PATENT DOCUMENTS

| KR | 1355678 B1 * | 1/2014 | ............ A61L 15/22 |
|---|---|---|---|
| KR | 10-1490140 | 2/2015 | |
| KR | 2015-0116990 | 10/2015 | |
| KR | 10-1355678 | 12/2016 | |

OTHER PUBLICATIONS

Gorna et al. (Abstract of: J Biomed Mater Res 2002;60(4):592-606) 2 pages (Year: 2002).*
Khajavi et al. (Scientia Iranica F 2012;19(6):2029-2034) (Year: 2012).*
International Search Report and Written Opinion issued in International Patent Application No. PCT/KR2017/003298, dated Jun. 23, 2017.

* cited by examiner

[Fig.1]
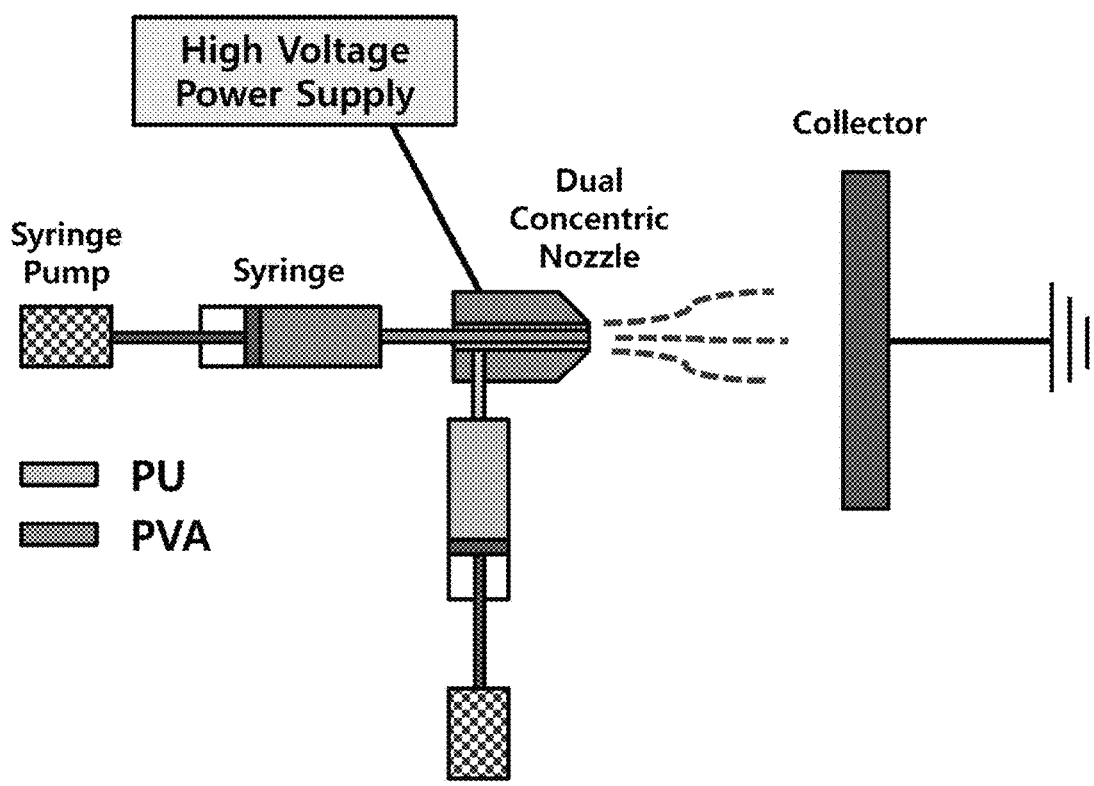
[Fig.2a]
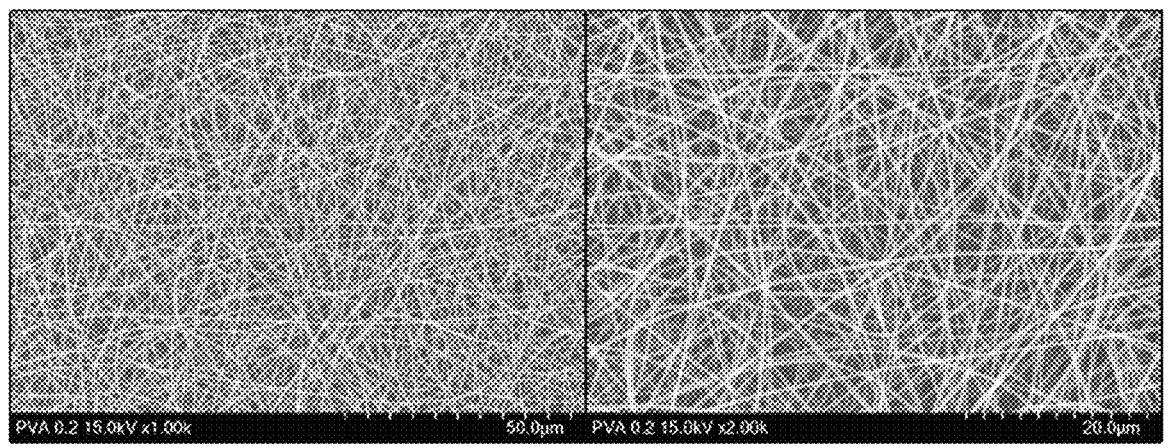

[Fig.2b]
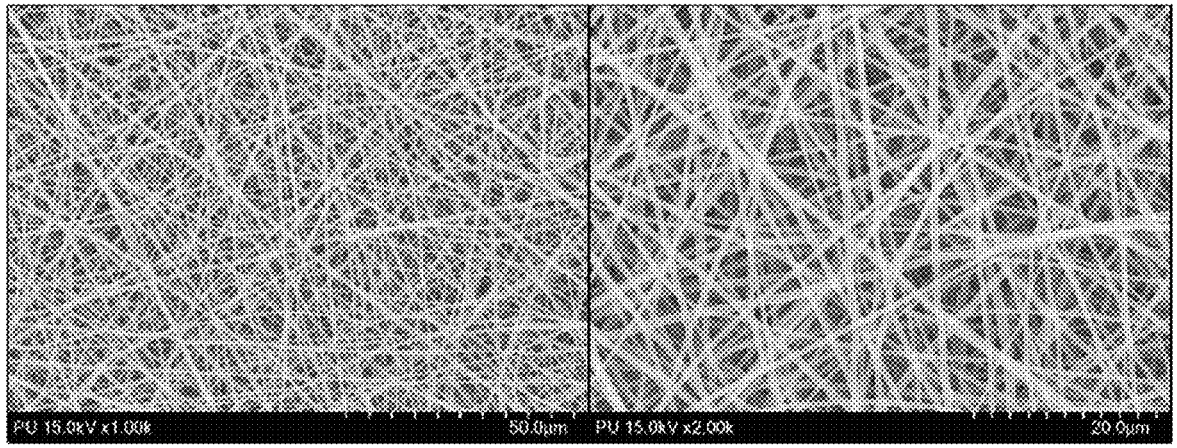
[Fig.3]
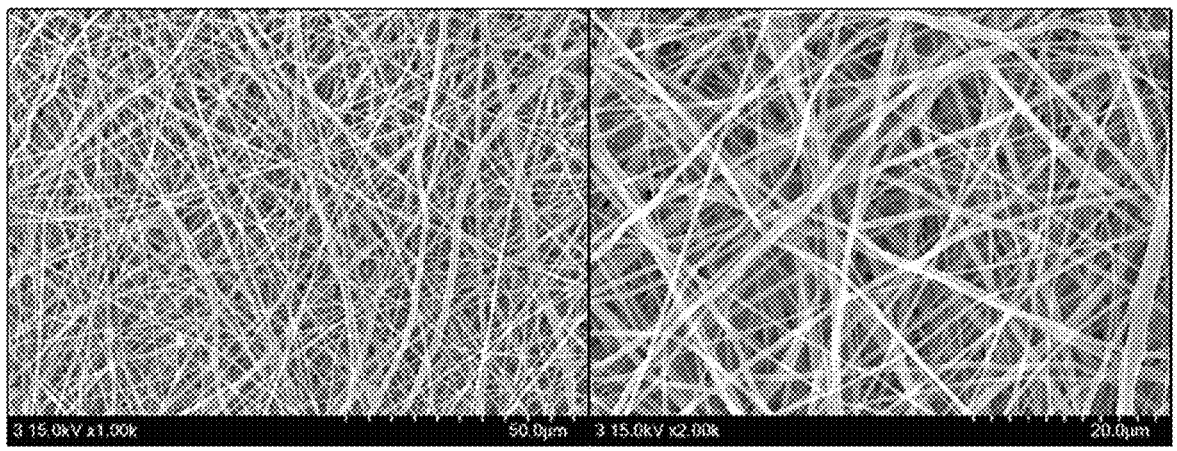
[Fig.4a]
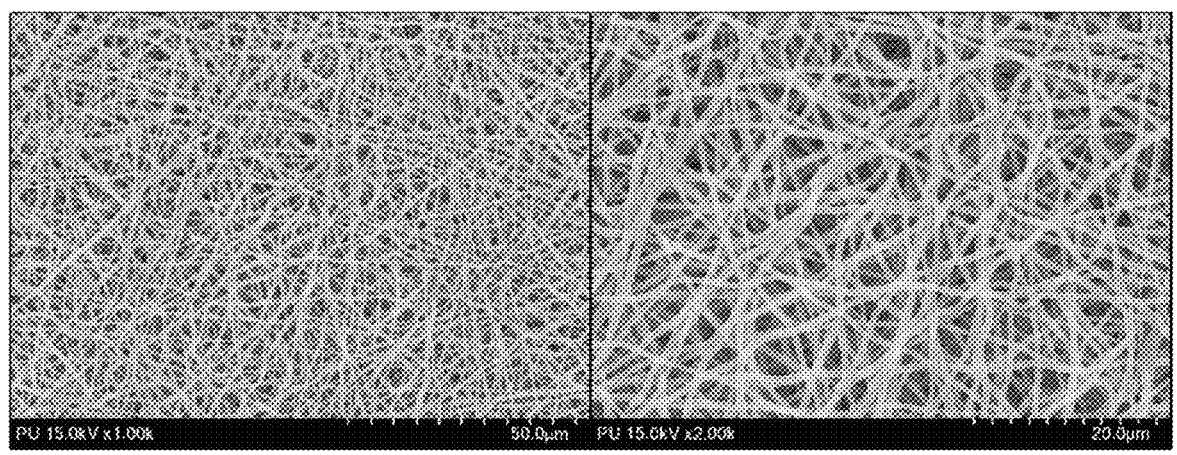

[Fig.4b]
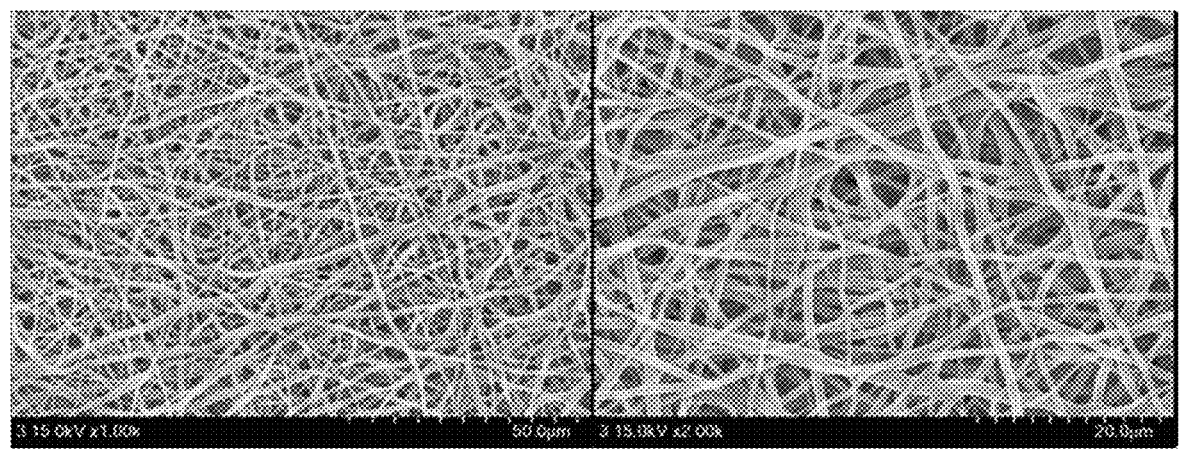
[Fig.5]
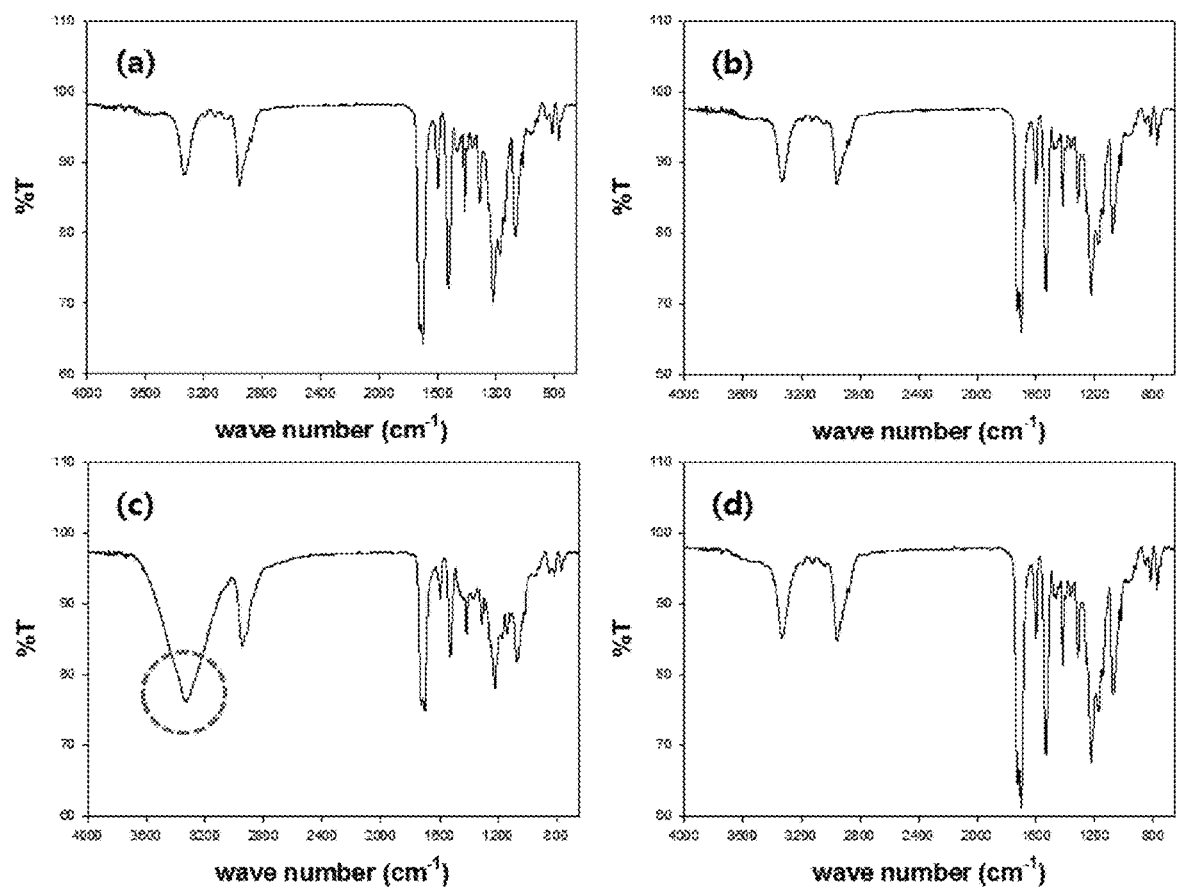

[Fig.6]
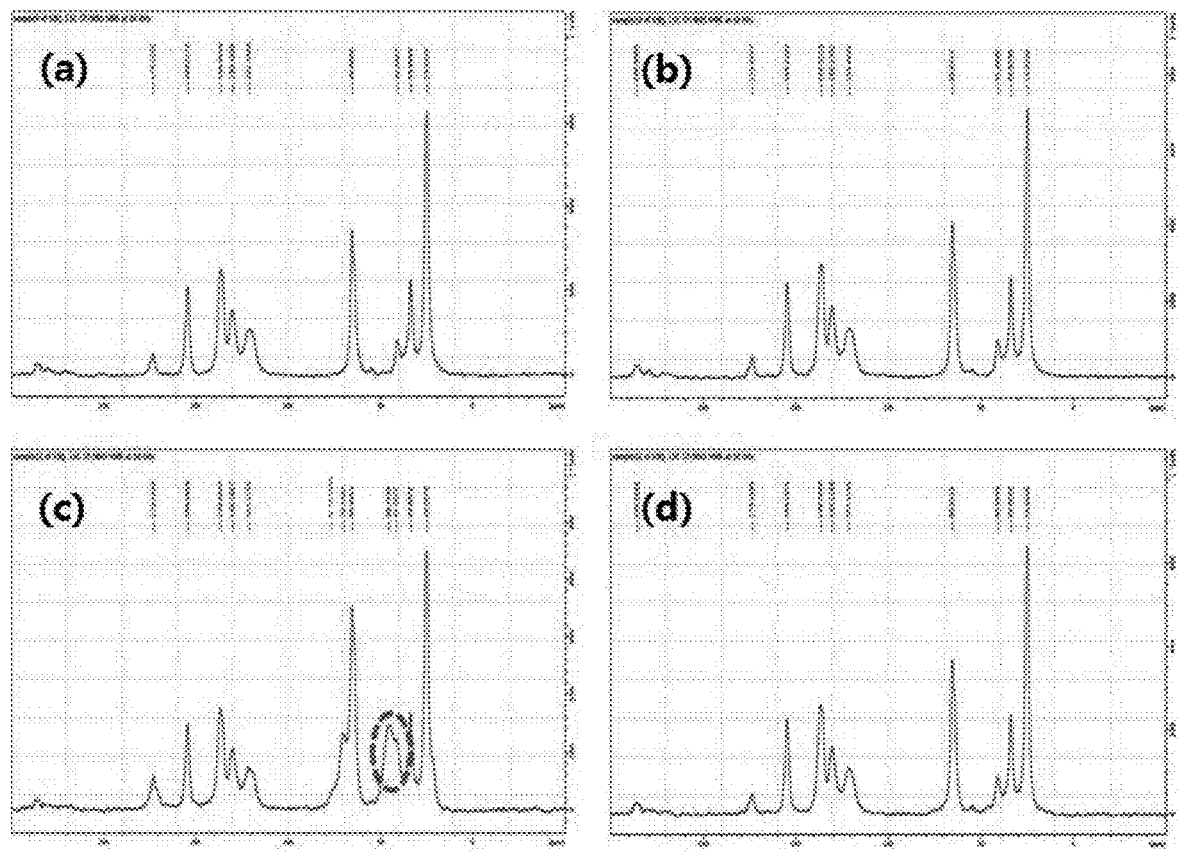

[Fig.7a]
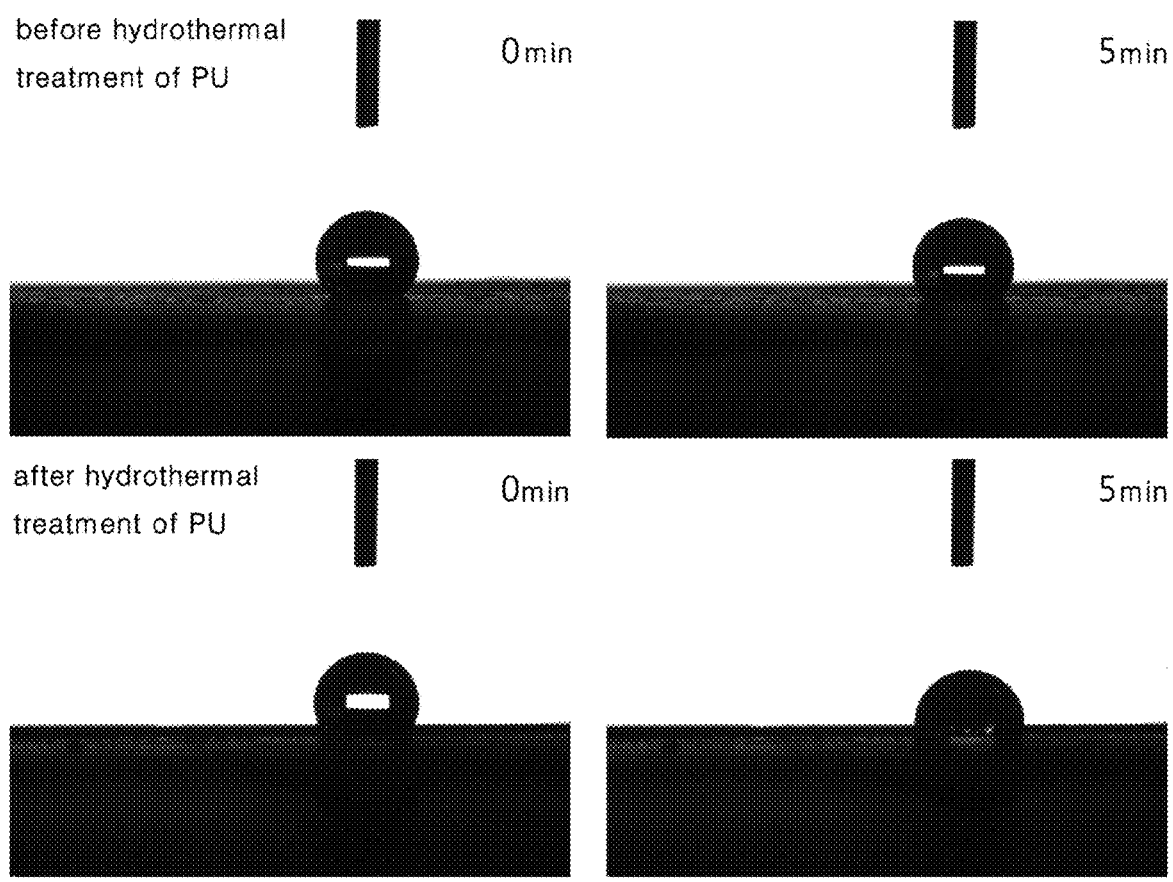

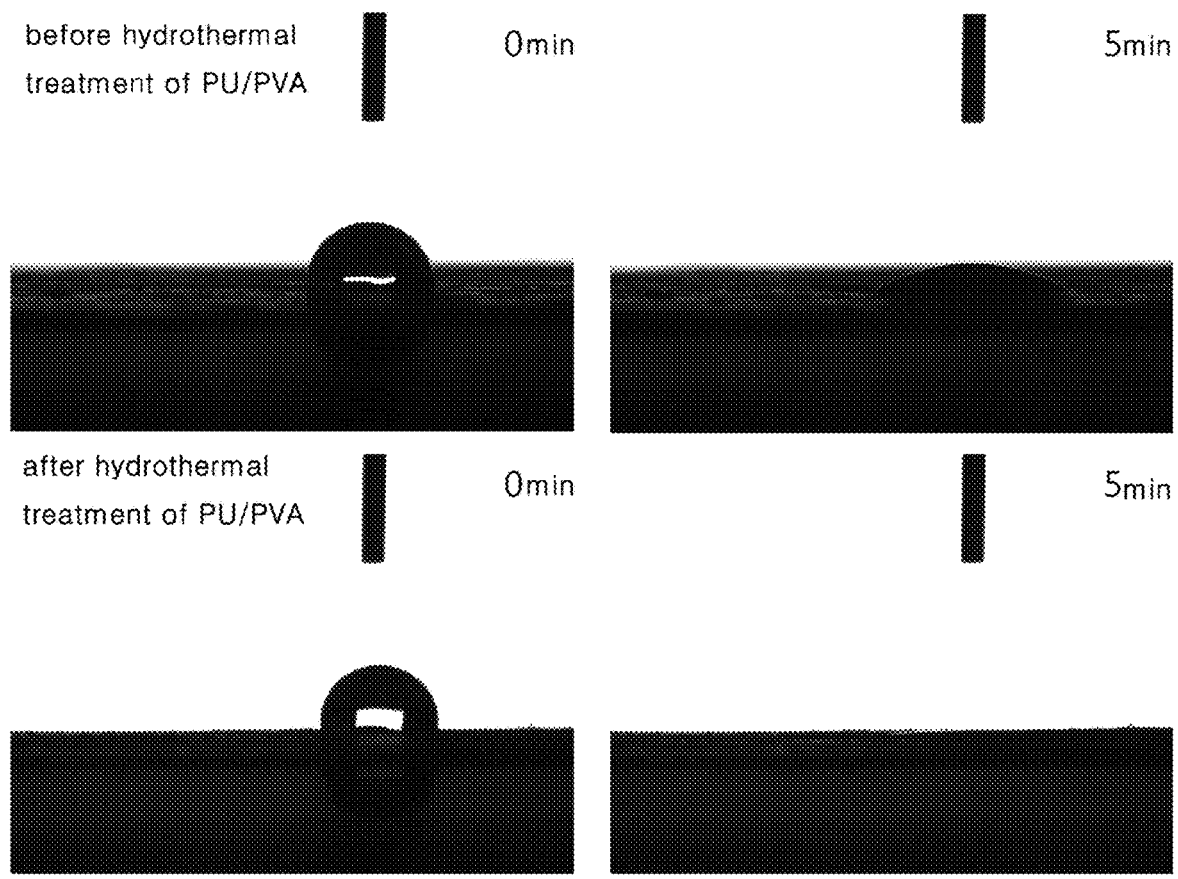

[Fig.8]
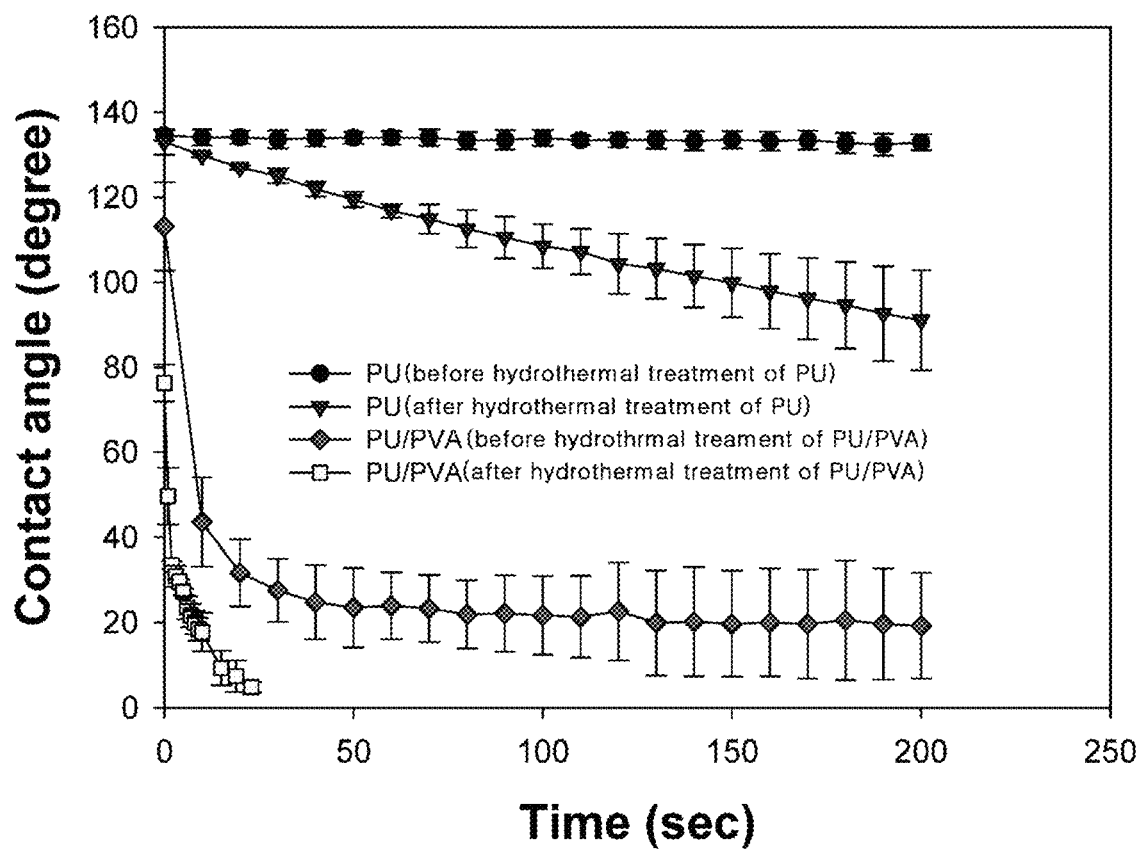

HYDROPHILIC POLYURETHANE NANOFIBER AND METHOD FOR MANUFACTURING SAME

CROSS-REFERENCE TO RELATED APPLICATIONS

This application is a national phase under 35 U.S.C. § 371 of International Application No. PCT/KR2017/003298, filed Mar. 28, 2017, which claims the benefit of priority to Korean Patent Application No. 10-2016-0037731 filed on Mar. 29, 2016 in the Korean Intellectual Property Office, the entire contents of each of which are hereby incorporated by reference in their entirety.

BACKGROUND

1. Technical Field

The present disclosure describes a method for producing polyurethane nanofibers having improved hydrophilicity by producing polyurethane/water-soluble polymer blend nanofiber using coaxial-electrospinning and then dissolving and removing the water-soluble polymer in water.

2. Related Art

Electrospinning is mainly used for dissolving polymers in solution or by directly dissolving them to produce fibers with diameters of a few micrometers to a few nanometers. The nanofiber produced using electrospinning has a much larger specific surface area than a micro-fiber, has a smaller pore than a micro-fiber, has a freely adjustable pore size, strong surface adsorption, and selective permeability to the material. In addition, different nanofibers composed of different materials may advantageously be compounded with each other. Further, the smaller the diameter of the nanofiber, the larger the ratio of surface area to volume of the nanofiber. The large surface area sufficiently constitutes the wet state. Because nanofibers have a three-dimensional structure similar to the structure of the extracellular matrix, nanofibers facilitate drug release at the wound site and wound regeneration is effective using the nanofibers. The nanofiber produced by electrospinning may be used for a wide range of applications, including filter materials, fiber materials, secondary electrode materials, tissue engineering supports, energy storage materials, fiber reinforced nanocomposites, sensor fibers, electro-optic fiber materials, and the like.

Polyurethane (PU) is produced by the reaction of a polyisocyanate (—NCO) with a polyol (—OH). Due to the excellent properties of urethane only, PU may be used in a variety of applications. For example, PU may be used to produce products that are always available in our daily life, such as shoes, sofas, beds, cars, refrigerators, building materials. Further, the application of the PU is expanding to include eco-friendly and medical functional materials including biofilters for organic waste treatment, blood and plasma filters, and wetting dressings.

However, when a hydrophobic polymer material is applied to a water treatment filter or a blood filter, contamination and clogging due to adsorption of chemical or biological components including various organic compounds, proteins and microorganisms may occur. In order to prevent this, the improvement of the hydrophilicity of the polymer filter is becoming a key technology.

PU nanofiber obtained by electrospinning polyurethane has been tried to be applied as various filters. However, a similar problem arises due to the hydrophobicity of such PU nanofibers. Particularly, in the case of nanofibers of PU, clogging is pointed out as a serious problem because the PU nanofiber has relatively finer pores than a general filter membrane. Further, polyurethane is produced in the form of porous foam, and is commercialized as a typical wettable dressing material. When the PU nanofiber is produced, the water absorption on the surface of the hydrophobic nanoweb is remarkably lowered than that of the porous foam, so that it is difficult to expect a wettable wound healing effect using the PU nanofiber. Therefore, to apply polyurethane in the form of nanofiber to wound dressings, it is essential to improve the hydrophilicity of the polyurethane nanofiber.

In order to improve the hydrophilicity of the hydrophobic polymer structure, introduction of a hydrophilicity group on the surface by plasma treatment, coating of a hydrophilicity substance on the surface, and a combination thereof are generally used. However, in the case of the plasma treatment, the effect of improving the hydrophilicity is insignificant. In order to improve the hydrophilicity, treatment conditions may be made severe. This may cause the mechanical properties to be deteriorated. Further, when a hydrophilic polymer or the like is coated on the surface of a nanofiber structure such as a nanoweb, clogging of the pores occurs, making it difficult to use the nanofiber structure as a filter. Furthermore, most hydrophobic polymers, including most polyurethanes, are incompatible with hydrophilic polymers. During mixing of them, precipitation or other phase separation phenomenon occurs, thereby forming a non-uniform solution. As a result, it is practically impossible to produce a uniform nanofiber by electrospinning the mixed solution between two hydrophilic and hydrophobic polymers.

The present inventors have studied a method for improving the hydrophilicity of PU in order to overcome the problems of the hydrophobic PU nanofiber and to solve the problems of the prior art as described above. These study results show that when nanofibers are produced by coaxial-electrospinning hydrophilicity polymers and hydrophobic PUs that are not blend together, blend nanofibers of the hydrophilicity polymer and the PU may be produced. Furthermore, it was found rather than as an unexpected result that the produced PU nanofiber had better hydrophilicity by dissolving and removing the hydrophilicity polymer component in the blend nanofiber in water. These findings led to the completion of the present disclosure.

SUMMARY

The purpose of the present disclosure is to provide a method for producing PU nanofibers with significantly improved hydrophilicity by producing water-soluble polymer/PU blend nanofiber by coaxial-electrospinning water-soluble polymer and hydrophobic PU, which are incompatible with each other, and, subsequently, dissolving and removing the water-soluble polymer in the blend nanofiber in water.

The purposes of the present disclosure are not limited to the above-mentioned purposes, and, rather, other purposes and advantages of the present disclosure, as not mentioned above, may be understood from the following descriptions. Other objects and advantages will be more clearly understood by reference to the embodiments of the present disclosure. Further, it will be readily appreciated that these objects and advantages of the present disclosure may be realized by features and combinations thereof recited in the claims.

In one aspect, the present disclosure provides a method for producing hydrophilic polymer nanofibers: the method comprising: providing hydrophilic polymer solution dissolved in water; providing hydrophobic polymer solution dissolved in organic solvent; injecting the hydrophilic polymer solution and the hydrophobic polymer solution into an inner nozzle and an outer nozzle for coaxial-electrospinning respectively or into an outer nozzle and an inner nozzle for coaxial-electrospinning respectively and, performing coaxial-electrospinning; and hydrothermally-treating the coaxial-electrospun nanofiber to remove the hydrophilicity polymer therefrom.

According to the present disclosure, coaxial electrospinning is a method including independently injecting two polymer solutions into the inner and outer nozzles, which are separated from each other and electrospinning the solutions. The two solutions come out of the two nozzles and are spun and stretched to form a core-sheath type nanofiber. When using the double nozzles, it is possible to produce a nanofiber having a dual structure by applying different polymers. In particular, it is advantageous to produce a blended nanofiber by spinning the two polymer solutions which are incompatible with each other.

In one embodiment of the method, the hydrophilic polymer solution and the hydrophobic polymer solution are injected into the inner nozzle and the outer nozzle for coaxial-electrospinning respectively. In this way, the hydrophilic polymer is positioned in the core and the hydrophobic polymer is located in the shell, thereby producing a core/shell type hydrophilic/hydrophobic mixed fiber.

In one embodiment of the method, the hydrophobic polymer is polyurethane. Polyurethane is a polymer that is relatively difficult to disperse in water. According to the present disclosure, the polyurethane fiber has relatively hydrophilicity. In this connection, the term "relatively" may mean higher hydrophilicity than that of polyurethane nanofiber without treatment according to the present disclosure, and may mean improved hydrophilicity as compared with a blended fiber with hydrophilic polymer.

In one embodiment of the method, the organic solvent includes at least one organic solvent selected from a group consisting of DMF, DMAc, MEK, and THF.

In one embodiment of the method, the hydrophilic polymer includes at least one polymer selected from a group consisting of polyvinyl alcohol (PVA), polyvinyl pyrrolidone (PVP), polyethylene oxide (PEO), polyacrylic acid (PAA), poly (sodium acrylate), carboxymethylcellulose, sodium alginate (SA), chitosan, pullulan, starch, gelatin and collagen.

In one embodiment of the method, the hydrothermal treatment is hydrothermal treatment using distilled water at 0 to 100° C.

In another aspect, the present disclosure provides a hydrophilic polyurethane nanofiber web, wherein polyurethane nanofiber strands define pores, wherein each of the polyurethane nanofiber strands has a serpentine shape. The pores may be formed in the core/shell nanofiber, with the hydrophilic polymer of the core being removed. In one embodiment of the hydrophilic polyurethane nanofiber web, each of the polyurethane nanofiber strands is hollow.

In still another aspect, the present disclosure provides a blood or plasma filter or a water treatment filter including the hydrophilic polyurethane nanofiber web of claim as defined above.

In still another aspect, the present disclosure provides a wettable dressing material including the hydrophilic polyurethane nanofiber web as defined above.

The water-soluble polymer/PU blend nanofiber according to the present disclosure is produced by coaxial-electrospinning. The PU nanofiber obtained by dissolving the water-soluble polymer component in water and removing the same from the water-soluble polymer/PU blend nanofiber has the property of decreasing the contact angle and increasing the water absorption. As a result, it was confirmed that the hydrophilicity of the resulting nanofiber was significantly increased.

The hydrophilic PU nanofiber produced by the present disclosure may be applied to water treatment and blood filters. Due to the remarkable improvement in hydrophilicity, contamination and clogging due to adsorption of chemical/biological components such as various organic compounds, proteins and microorganisms may be suppressed. Thus, the resulting nanofiber may be used in various fields such as medical materials such as wettable wound dressings, health care materials, and outdoor materials.

Further, carrying out coaxial-electrospinning of various kinds of polymers other than the polymers proposed in the present disclosure and dissolving and removing any one of the polymers may modify the hydrophobicity of the nanofiber into the hydrophilicity via a physical modification method rather than a chemical modification method of the hydrophobic polymer nanofiber.

BRIEF DESCRIPTION OF THE DRAWINGS

FIG. 1 is a schematic representation of a coaxial-electrospinning process for producing PVA/PU blend nanofiber in accordance with the present disclosure.

FIG. 2 shows scanning electron microscope (SEM) photographs (a) and (b) of PVA nanofiber and PU nanofiber respectively.

FIG. 3 is a SEM image of PVA/PU blend nanofiber.

FIG. 4 shows SEM images (a) and (b) of hydrothermal-treated PU and hydrothermal-treated PVA/PU blend nanofiber respectively.

FIG. 5 shows: (a) indicates a result of infrared (IR) spectroscopic analysis of PU nanofiber before hydrothermal treatment and (b) indicate a result of infrared (IR) spectroscopic analysis of PU nanofiber after hydrothermal treatment; (c) indicate a result of Infrared (IR) spectroscopic analysis of PVA/PU blend nanofiber before hydrothermal treatment, and (d) indicates a result of infrared (IR) spectroscopic analysis of PVA/PU blend nanofiber after hydrothermal treatment.

FIG. 6 shows: (a) indicates a result of $13^C$-solid nuclear magnetic resonance ($13^C$-solid NMR) spectroscopic analysis of PU nanofiber before hydrothermal treatment; (b) indicates a result of $13^C$-solid nuclear magnetic resonance ($13^C$-solid NMR) spectroscopic analysis of PU nanofiber after hydrothermal treatment; (c) indicates a result of $13^C$-solid nuclear magnetic resonance ($13^C$-solid NMR) spectroscopic analysis of PVA/PU blend nanofiber before hydrothermal treatment; (d) indicates a result of $13^C$-solid nuclear magnetic resonance ($13^C$-solid NMR) spectroscopic analysis of PVA/PU blend nanofiber after hydrothermal treatment.

FIGS. 7a and 7b show an image of a contact angle of PU and PVA/PU blend nanofibers respectively.

FIG. 8 shows contact angle measurement results of PU and PVA/PU blend nanofibers over time.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims. The same reference numbers in different figures denote the same or similar elements, and as such perform similar functionality.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The PVA/PU blend nanofiber was produced by coaxial-electrospinning a variety of water-soluble polymer solutions including PVA, which is the most representative water-soluble polymer, and PU solutions dissolved in organic solvents. Then, the resulting PVA/PU blend nanofiber is hydrothermally treated to remove the PVA. This allows the applicants to produce PU nanofibers with improved hydrophilicity.

Accordingly, in accordance with the present disclosure, a method for producing a PU nanofiber with improved hydrophilicity, which comprises the following steps:

(a) producing PVA electrospinning solution by dissolving water-soluble polymer containing PVA in distilled water;

(b) dissolving PU in an organic solvent to produce a PU electrospinning solution;

(c) inserting the water-soluble polymer electrospinning solution and the PU electrospinning solution into first and second syringes respectively;

(d) applying a voltage to electrodes connected to the first and second syringes respectively, discharging and coaxial-electrospinning the water-soluble polymer and the PU solution using a dual coaxial-nozzle to form a water-soluble polymer/PU nanofiber;

(e) dissolving and removing the water-soluble polymer component in the water-soluble polymer/PU nanofiber in water; and (f) vacuum-drying the PU nanofiber with water-soluble polymer removed.

In the step (a), the water-soluble polymer may be a synthetic polymer such as PVA, PVP, PEO, PAA and PSA; cellulose derivatives including CMC; SA, CS and derivatives thereof; polysaccharide-based polymers such as pullulan and starch; protein-based polymers such as gelatin and collagen; or a mixture thereof.

In the step (b), the organic solvent may be a mixed solvent containing one or more organic solvents selected from the group consisting of DMF, DMAc, MEK, and THF.

In the step (d), the applied voltage may be 1 kV to 100 kV, and the ejection speed may be adjusted according to the type of the polymer and the difference in voltage applied to the electrode.

In step (e), removal of the water-soluble polymer by hydrothermal treatment may be performed in distilled water at 0 to 100° C. The present disclosure is not limited to these temperatures. Other temperatures that may remove water-soluble polymers are also available.

In accordance with one embodiment of the present disclosure, coaxial-electrospinning of the water-soluble polymer PVA and polar organic solvent-soluble PU was performed to produce a PVA/PU blend nanofiber. The resulting PVA/PU blend nanofiber was subjected to hydrothermal treatment to remove PVA to produce the PU nanofiber. Changes in the hydrophilicity of these intermediate and final products were determined by measuring the structure, component properties, and contact angle thereof.

As a result of observing SEMs of nanofibers resulting from spinning of PVA and PU solution, and the PVA/PU blend nanofiber, PVA and PU nanofibers were found to have a diameter of several hundred nanometers and uniform thickness in the optimal electrospinning condition. The diameter of PVA/PU blend nanofiber increased. Further, removal of the water-soluble PVA via hydrothermal treatment reduces the contact angle of the resulting PU nanofiber, and, thus, it rapidly absorbs water over time Hereinafter, the present disclosure is described in more detail in the following examples, which are merely illustrative of the content of the present disclosure and are not intended to limit the technical scope of the present disclosure.

Example 1

PVA Nanofiber Production by Electrospinning

PVA (Mw 88,000, 99+% hydrolyzed, OCI, Korea) was injected into distilled water at 10% (w/v) to form a first solution. The first solution was stirred at 80 degree C. for 4 hours to completely dissolve the PVA to produce a PVA electrospinning solution. The PVA electrospinning solution was subjected to electrospinning at a voltage of 12 kV, a distance of 15 cm, and a discharge rate of 0.2 ml/h to produce a PVA nanofiber.

Example 2

PU Nanofiber Production by Electrospinning

PU (polyester-based thermoplastic polyurethane, Lubrizol, USA) was injected into DMF at 13 wt % to form a second solution. The second solution was stirred at room temperature for 4 hours to completely dissolve the PU to form PU electrospinning solution, which, in turn, was subjected to electrospinning at a voltage of 12 kV, a distance of 15 cm and a discharge rate of 0.3 ml/h to produce PU nanofiber.

Example 3

Hydrothermal-Treated PU Nanofiber Production

The PU nanofiber produced in example 2 was placed in tertiary distilled water at 80° C. and the distilled water was slowly stirred for 24 hours. The distilled water was vacuum-dried at room temperature for 24 hours to produce hydrothermal-treated PU nanofiber.

Example 4

Production of PVA/PU blend nanofiber by coaxial-electrospinning

PVA electrospinning solution was prepared by dissolving PVA (Mw 88,000, 99+% hydrolyzed, OCI, Korea) in distilled water at 10% (w/v). Then, PU (polyester-based thermoplastic polyurethane, Lubrizol, USA) was added to DMF at 13 wt %, and DMF was stirred at room temperature for 4 hours to completely dissolve PU to produce PU electrospinning solution. Then, the two spinning solutions produced above were subjected to coaxial-electrospinning to produce a PVA/PU blend nanofiber (see FIG. 1). In this connection, the coaxial-electrospinning was executed under the conditions of a voltage of 20 kV, a distance of 15 cm, a discharge rate of PVA (core) of 0.2 ml/h and a discharge rate of PU (shell) of 0.3 ml/h.

Example 5

Hydrothermal-Treated PVA/PU Nanofiber Production

The PVA/PU blend nanofiber produced in Example 4 was placed in a third distilled water at 80° C. and the distilled water was slowly stirred for 24 hours. Then, the solution was vacuum-dried at room temperature for 24 hours. This yielded hydrothermal-treated PVA/PU nanofiber.

Morphological Observation

Platinum was coated on the nanofiber produced by the above method. The external morphological structure of the coated nanofibers was observed using SEM. FIGS. 2 (a) and (b) are SEM images of PU nanofibers of PVA nanofibers, respectively. FIG. 3 is a SEM image of a PVA/PU blend nanofiber. The thickness of the PVA/PU blend nanofiber was slightly increased when comparing the SEM photographs of PVA nanofiber and PU nanofiber with the SEM photograph of PVA/PU blend nanofiber.

FIG. 4 shows SEM images (a) and (b) of hydrothermal-treated PU and hydrothermal-treated PVA/PU blend nanofiber respectively. In this connection, the nanofibers were hydrothermal-treated in distilled water at 80° C. for 24 hours and dried in a vacuum for 12 hours. There was no significant change in fiber thickness before and after hydrothermal treatment. Curling is generally exhibited. This is probably due to the removal of residual solvent and PVA component during hydrothermal treatment, and the heat shrinkage of PU by heating.

These results suggest that hydrothermal treatment of PU nanofibers and PVA/PU blend nanofibers may lead to nanostructure changes in the nanofiber, and the degree of the change is considered to be larger in the PVA/PU blend nanofiber due to the fact that the residual solvent and PVA with high molecular weight are simultaneously released therefrom.

IR Spectroscopy Results

IR spectroscopy was performed to analyze the compositions of PU nanofiber and PVA/PU blend nanofiber. FIG. 5 shows: (a) indicates a result of infrared (IR) spectroscopic analysis of PU nanofiber before hydrothermal treatment and (b) indicate a result of infrared (IR) spectroscopic analysis of PU nanofiber after hydrothermal treatment; (c) indicate a result of Infrared (IR) spectroscopic analysis of PVA/PU blend nanofiber before hydrothermal treatment, and (d) indicates a result of infrared (IR) spectroscopic analysis of PVA/PU blend nanofiber after hydrothermal treatment. PU nanofiber showed PU characteristic absorption peaks at 3400 to 3200 $cm^{-1}$ and at 1800 to 1630 $cm^{-1}$, and no peak change due to absence or presence of hydrothermal treatment was observed. In the case of PVA/PU blend nanofiber, a strong characteristic absorption peak of —OH group was observed at 3650 to 3000 $cm^{-1}$ together with PU characteristic absorption peak due to the influence of PVA, but this strong characteristic absorption peak disappeared after hydrothermal treatment. This may confirm that PVA was removed and only PU remained via the hydrothermal treatment.

$13^C$-Solid NMR Spectroscopy Results $13^C$-solid NMR spectroscopy was performed for the analysis of PU nanofiber and PVA/PU blend nanofiber components. FIG. 6 shows: (a) indicates a result of $13^C$-solid nuclear magnetic resonance ($13^C$-solid NMR) spectroscopic analysis of PU nanofiber before hydrothermal treatment; (b) indicates a result of $13^C$-solid nuclear magnetic resonance ($13^C$-solid NMR) spectroscopic analysis of PU nanofiber after hydrothermal treatment; (c) indicates a result of $13^C$-solid nuclear magnetic resonance ($13^C$-solid NMR) spectroscopic analysis of PVA/PU blend nanofiber before hydrothermal treatment; (d) indicates a result of $13^C$-solid nuclear magnetic resonance ($13^C$-solid NMR) spectroscopic analysis of PVA/PU blend nanofiber after hydrothermal treatment. In FIG. 6, PU characteristic peaks could be found at 24-41 ppm, 65 ppm, 120-136 ppm, 154 ppm before and after hydrothermal treatment of the PU nanofiber. Before the hydrothermal treatment of the PVA/PU blend nanofiber, PVA characteristic peaks could be observed at around 45 ppm and 70 ppm. After hydrothermal treatment of PVA/PU blend nanofiber, PVA characteristic peaks were not observed at around 45 ppm and 70 ppm. This could confirm that PVA was removed and only PU remained.

Contact Angle Measurement Result

In order to evaluate the hydrophilicity of PU nanofiber and PVA/PU nanofiber, the contact angle between water and nano-web surface was measured at temperature 21° C. and humidity 25%±20 using a contact angle measurement device.

In the case of a pure PVA nanofiber, upon contact with moisture, the PVA nanofiber dissolves. Therefore, the angel was not measured. FIG. 7(a) shows the contact angle of PU nanofiber before hydrothermal treatment. The initial contact angle was 133.1°, and after 5 minutes, the contact angle was 130.4°. After hydrothermal-treatment, the initial contact angle of the PU nanofiber was 126°, and after 5 minutes, it showed a contact angle of 78.2°. FIG. 7(b) shows the contact angle of PVA/PU blend nanofiber before hydrothermal treatment. The initial contact angle was 109.8°, and after 5 minutes, it was 19.8°. In the PVA/PU blend nanofiber after hydrothermal-treatment, the initial contact angle was 82.0° and the water was fully absorbed into the fiber before 30 seconds passed. Therefore, the contact value was no longer measured.

The hydrothermal treatment of the PU nanofiber is thought to result in a fine pore in the nanofiber due to the removal of the residual solvent and an increase in water absorption due to the capillary phenomenon. In the case of PVA/PU blend nanofiber, the contact angle was greatly reduced due to the presence of water-soluble polymer PVA. As may be seen in FIG. 8, the rapid decrease in contact angle due to the dissolution of PVA as a water-soluble polymer is observed, and the decrease in the contact angle may be observed to slow down after a certain amount of PVA has been dissolved.

In the case of the hydrothermal-treated PVA/PU blend nanofiber, the PVA was removed and only the PU remained, but the initial contact angle was lowest and the absorption rate was the fastest so that the water was completely absorbed before 30 seconds. Thus, the measurement of the contact angle was not performed. This is thought to be due to the greatest increase in water uptake due to increased micro-space generation and associated capillary phenomena due to the removal of PVA and residual solvent via the hydrothermal treatment.

Blending a hydrophilic polymer PU with a water-soluble polymer such as PVA incompatible with the PU via the coaxial-electrospinning is a modification method that may impart hydrophilicity. However, when the nanofiber is used as water treatment, plasma filters or wetting wound dressings, the water-soluble polymer components are dissolved and absorbed into the treatment liquid, blood, and skin, resulting in side effects. In order to prevent this situation, an insolubilization process of water-soluble polymer such as crosslinking or crystallization may additionally required.

According to the present disclosure, water-soluble polymers blended with PU are removed exclusively by dissolving in water, resulting in physical changes within the nanofiber, resulting in a superior hydrophilicity compared to the case in which the water-soluble polymer remains, thereby to bring about an improvement in hydrophilicity.

The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A method for producing a polyurethane nanofiber having hydrophilic and water-absorptive properties from a hydrophobic polyurethane, the method comprising:
    providing a polyvinyl alcohol (PVA) solution comprising a PVA dissolved in water;
    providing a hydrophobic polyurethane solution comprising a hydrophobic polyurethane dissolved in organic solvent;
    injecting the PVA solution and the hydrophobic polyurethane solution into an inner nozzle and an outer nozzle for coaxial-electrospinning, respectively, and, performing coaxial-electrospinning to produce a coaxial-electrospun nanofiber comprising the PVA and the hydrophobic polyurethane; and
    hydrothermally-treating the coaxial-electrospun nanofiber to remove the PVA therefrom and to produce the polyurethane nanofiber having hydrophilic and water-absorptive properties,
    wherein the produced polyurethane nanofiber has a lower water contact angle and higher water absorption when compared with the coaxial-electrospun nanofiber prior to hydrothermal treatment.

2. The method of claim 1, wherein the organic solvent includes at least one organic solvent selected from a group consisting of DMF, DMAc, MEK, and THF.

3. The method of claim 1, wherein the hydrothermal treatment is hydrothermal treatment using distilled water at 0 to 100° C.

* * * * *